United States Patent [19]

Rawls et al.

[11] Patent Number: 4,572,920
[45] Date of Patent: Feb. 25, 1986

[54] FLUORIDE INTERPOLYMERIC RESIN

[75] Inventors: Henry R. Rawls, New Orleans; Barbara F. Zimmerman, Metairie, both of La.

[73] Assignee: Research Corporation, New York, N.Y.

[21] Appl. No.: 700,847

[22] Filed: Mar. 20, 1985

Related U.S. Application Data

[63] Continuation-in-part of Ser. No. 461,026, Jan. 26, 1983, Pat. No. 4,515,910.

[51] Int. Cl.$^4$ .................... A61K 7/18; C08L 27/12
[52] U.S. Cl. .................... 523/115; 106/35; 424/151; 523/116; 524/544; 260/998.11
[58] Field of Search ............ 260/998.11; 106/35; 424/151; 523/115, 116; 524/544

[56] References Cited

U.S. PATENT DOCUMENTS

| | | | |
|---|---|---|---|
| 3,341,505 | 9/1967 | Gander | 526/287 |
| 3,427,274 | 2/1969 | Cornell | 106/35 |
| 3,625,916 | 12/1971 | Newman | 524/434 |
| 3,925,895 | 12/1975 | Kliment et al. | 433/224 |
| 3,969,499 | 7/1976 | Lee et al. | 433/228 |
| 3,991,008 | 11/1976 | Temin et al. | 528/950 |
| 4,146,608 | 3/1979 | Ritchey | 424/147 |
| 4,155,890 | 5/1979 | Hofacker-Freifrau | 523/115 |
| 4,203,220 | 5/1980 | Cranfield | 433/228 |
| 4,515,910 | 5/1985 | Rawls et al. | 523/115 |

Primary Examiner—Ronald W. Griffin
Attorney, Agent, or Firm—Scully, Scott, Murphy & Presser

[57] ABSTRACT

An interpolymeric resin and composition therefrom is provided for treating teeth to prevent dental caries by forming a protective barrier and providing a source of fluoride ions for release adjacent to the surface of the tooth. The resin includes an anion-exchange-site bearing monomer carrying fluoride ions, an acrylic comonomer, a crosslinking monomer, and, optionally, a wetting/etching monomer. The resin may have a high degree of crosslinking which then may include filler material to form a composite composition.

31 Claims, 4 Drawing Figures

FLUORIDE RELEASE

FLUORIDE INTERPOLYMERIC RESIN

BACKGROUND OF THE INVENTION

This application is a continuation-in-part application of U.S. patent application Ser. No. 461,026 filed Jan. 26, 1983 now U.S. Pat. No. 4,515,910.

The present invention, which resulted from research conducted with the aid of funds granted by the National Institute of Health, relates to the art of dental health and, in particular, to interpolymeric resins useful in the treatment of teeth to prevent and/or inhibit dental decay.

In recent years, efforts in the area of preventive dental therapy have resulted in technology which provides a protective barrier for surfaces of teeth. This type of therapy, which generally includes a minimal removal of hard dental tissue cariously involved followed by restoration and/or sealing of the intact or acid-etched surface, has been shown to conserve health tooth tissue, reduce treatment time, and provide adequate protection against new caries.

Resins capable of setting (polymerizing and curing) in the oral environment play a primary role in effectuating such treatment. Depending on the nature of the desired results the resins employed in dental treatment should have specific characteristics such as good bonding properties, hardness, and non-degradation in the presence of water, etc. Since these preparations, which are variously characterized as sealant, restorative, and/or adhesive depending on the role they play in the particular treatment, must be capable of infiltrating an acid-etched surface and/or the porosity of carious tissue, the monomers must be highly fluid and have a strong affinity for mineral surfaces. Moreover, the resin must be able to solidify in thin dimensions under oral conditions.

In other dental and biomedical applications polymeric resins are used for constructing various removable and non-removable prosthetic devices and body-part replacements, and for various other purposes. Generally, depending on the desired results, the resins employed for these applications require little or no cross-linking and are not used as adhesives. In many applications in dentistry, prosthetic devices made from these materials interfere with good oral hygiene and, therefore, promote tooth decay and periodontal degradation. Materials for these applications can be formed and cured in situ, or they can be formed externally using an external source of energy such as light or heat. In this latter case, when the application of heat is utilized to effect curing an accelerating agent is not needed. Such materials are variously characterized as appliance resins, prosthetic resins, endodontic filling resins, resin cements, temporary restorative resins, veneering or utility resins, depending upon the role they play in dental or medical treatment. For example, U.S. Pat. No. 3,925,895 to Kliment, et al. describes an acrylic, hydrophilic root canal filling resin and U.S. Pat. No. 4,155,890 to Von Nostitz describes acrylic resins for both heat curing and accelerated curing in a patient's mouth to form prosthetic devices.

Dental resins are usually acrylic materials based on an ester of acrylic or methacrylic acid, typical monomers being methyl methacrylate or a diacrylate of 2,2-bis(p-hydroxyphenyl)-propane, known as BIS-(GMA) resins. The dental resin is normally used as a monomer or as a monomer/polymer mixture, i.e., an incompletely polymerized resin and polymerization is completed in situ when the resin has been placed in position on the dental tissue. Other types of clinically tolerated resins are known and used, e.g., in dentistry or orthopaedic surgery, all of which have polymerizable olefinic double bonds in the molecule. All such resins are available as monomers or monomer/polymer mixtures and include any necessary catalyst etc. so that, after the resin has been put in its final position, completion of polymerization occurs within a few minutes under ambient conditions.

U.S. Pat. No. 4,203,220 to Cranfield describes the use of a bifunctional bridging molecule for bonding dental resins, which are usually acrylic materials based on an ester of acrylic or methacrylic acid, to dental tissue. Specifically, this disclosure shows the use of alkylamino dihalotrazines which have a group that chemically reacts with the dental tissue and a reactive group that polymerizes with the dental resin.

U.S. Pat. No. 3,341,505 to Gander shows a film-forming composition resulting from polymerization of acrylic or methacrylic esters with certain acrylate or methacrylate amine containing monomers. The esters are of alkyl alcohols containing 1 to 12 carbon atoms, while the amine containing resins are typically reacted with acid ions such as fluoride, chloride, bromide, iodide and sulfate and organic sulfonates which are capable of being attached either directly or indirectly to form the amine salt. The resins can be used as a flexible water soluble film on the skin or as a cement composition for adhering dressings.

Further work in the dental area and, for that matter, in hard tissue technology in general has also provided methods of incorporating medicaments in sealants and-/or restorations and/or adhesives such that the medicaments are released from the host composition over a period of time. In U.S. Pat. No. 3,969,499 to Lee Jr., et al. a polyurethane composition containing a fluoride ion is used as a dental tissue sealant which also serves as a topical fluoride treatment for teeth. The composition used in the Lee, Jr., et al. '499 disclosure is a polymeric reaction product of a hydroxy-terminated butadiene prepolymer and a polyisocyanate reactant, as well as an aromatic polyol in one embodiment, while the source of the fluoride ions by a diffusion/dissolution mechanism.

Similarly, in U.S. Pat. No. 3,625,916 to Newman a "decay-preventing" cement is disclosed which includes primarily an acrylic resin of polymethyl methacrylate and polyethyl methacrylate having an inorganic fluoride. Once again, fluoride is released by a diffusion/dissolution mechanism.

As a result of the teachings in the art in general relative to the mechanism of release of fluoride ions, dissolution of the anti-caries components in adhesive or restorative host resins has been regarded as a necessity to effect topical application of the anti-caries agent.

By the present invention, however, an improved sealant/adhesive/restorative resin has been provided which is readily wettable to the teeth, sets rapidly under oral conditions in a thin layer, and effects topical fluoride release without the necessity of dissolving components of the resin.

Furthermore, the mechanism for the amount of, and the time of fluoride ion release is highly controllable.

SUMMARY OF THE INVENTION

According to the present invention there is provided a highly effective fluoride releasing acrylic interpolymer which delivers fluoride ions by means of a diffusion-controlled anion-exchange mechanism. The interpolymer is a reaction product of an anion-exchange-site bearing monomer which carries fluoride ions and a polymerizable acrylic monomer selected from alkyl acrylates and methacrylates wherein the alkyl group contains no more than about twelve (12) carbon atoms, and a crosslinking monomer. Anion-exchange-site bearing monomers useful herein include aminoalkylacrylates and aminoalkylmethacrylates. When used in dental applications, the amount of fluoride containing monomer included in the interpolymer should be an amount sufficient to provide a caries inhibiting amount of fluoride; up to no more than about 40% of the interpolymer.

In one embodiment of the invention the crosslinking comonomer effects a very high degree of crosslinking in the resulting resin, which can also be combined with a filler material such as silica or silanized silica to form a composition of matter for dental restoration. In order to effect a plastic-like composition to facilitate application to the teeth, a preformed polyalkylacrylate powder may be included with the resin.

While the present invention is presently contemplated as primarily useful as a method of preventing dental caries by impregnation, sealing or filling of the teeth with the disclosed interpolymers and compositions therefrom, or as a removable oral device for delivering fluoride, it is also believed that this invention is useful in bio-medical applications in general, such as bone cement. Accordingly, all such roles are considered to be within the scope of the present invention.

As a result of the present invention a rapid setting resin has been provided for use in dental applications which is highly wettable to the enamel surface of the teeth, strongly adhesive thereto, high in impact strength, and which delivers anti-caries fluoride ions to the adjacent tooth surfaces to inhibit the progression of caries in the area of such application.

It has also been discovered that high molecular weight acrylic materials or acrylic materials that are made up of large molecules such as those formed by the reaction of bis-phenol A, cyclic dicarboxylic acids such as cyclohexane or cyclohexene dicarboxylic acids or urethanes with acrylic acids or methacrylic acids, when copolymerized with the fluoride releasing acrylic monomer, result in long term fluoride ion release at relatively constant rates without crazing, brittleness or significant discoloration.

For a better understanding of the present invention, together with other and further objects, reference is made to the following description, taken in conjunction with the accompanying drawings, and its scope will be pointed out in the appended claims.

DETAILED DESCRIPTION OF THE INVENTION

Figure 1:
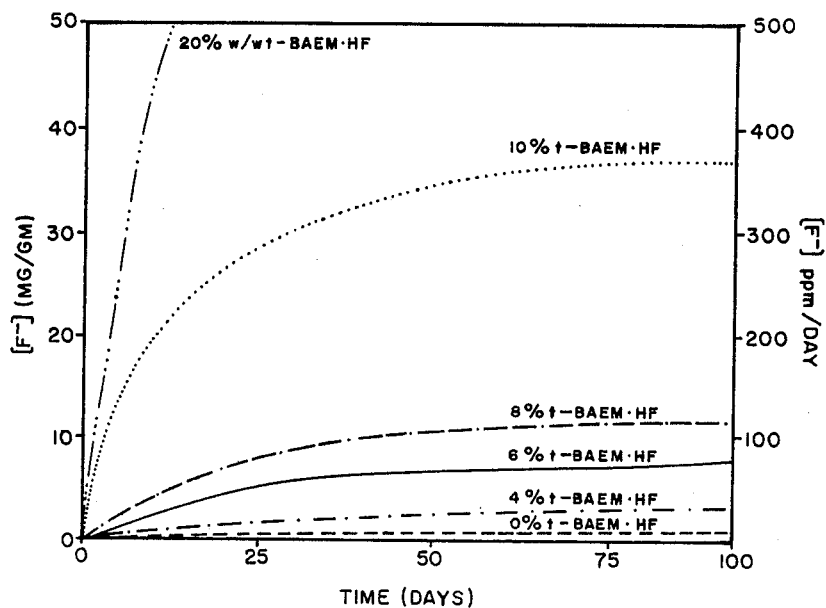
FIGS. 1 and 2 are graphs showing the cumulative fluoride ion release of acrylic interpolymers of the present invention.

By the present invention, it has been discovered that an interpolymer resin material highly effective for depositing on dental surfaces (especially those already having carious effects found therein) which also delivers fluoride ions in the oral cavity without the necessity of dissolving components from the deposited resin is provided by reacting a monomer having an anion exchange site carrying a fluoride ion with two or more polymerizable acrylic monomers, at least one of which is a crosslinker in the resulting resin reaction product.

The use of acrylic materials for dental resins is known. The alkyl radical of the methacrylate or acrylate useful herein contains up to about 12 carbon atoms and preferably contains from 1 to 5 carbon atoms. Some examples of methacrylates suitable for use in the present invention include methyl methacrylate, ethyl methacrylate, isopropyl methacrylate, butyl methacrylate, capryl methacrylate, palmityl methacrylate, stearyl methacrylate, lauryl methacrylate, 2,2-Bis[4-(2-hydroxy-3-methacroyloxypropoxy)phenyl]propane (Bis-GMA), 2-hydroxyethyl methacrylate (HEMA), and/or 1,3-butyleneglycol-dimethacrylate (BGD). Similarly, acrylate esters having the same alkyl radicals as those of the above methacrylates may be used. Additionally, various bisphenol A derivatives of acrylic and methacrylic acid can be employed as the acrylic material such as those set forth by Ruyter and Sjovik, Acta Odontol. Scand. 1981, 39, pp. 133–146 (hereinafter Ruyter, et al.) which are incorporated herein by reference; such as 2,2-Bis[4-methacroyloxyphenyl]propane (Bis-MA); (Bis-GMA); 2,2-Bis[4-(2-methacroyloxy-ethoxy)phenyl]propane (Bis-EMA); 2,2-Bis[4-(3-methacroyloxy-propoxy)-phenyl]propane (Bis-PMA); the dimethacrylate derivative of 1,2-cyclohexanedicarboxylic acid (c-HaDMA), the dimethacrylate derivative of 4-cyclohexene-1,2-dicarboxylic acid (c-HeDMA), the formulae for the latter two compounds given in Ruyter, et al.; and dimethacrylate monomers containing urethane groups such as UEDMA and TUDMA, the structures of the latter two compounds being set forth in Ruyter, et al. Other acrylic monomers selected for use in the present invention because, among other things, of their respective properties, especially as crosslinking monomers, include but are not limited to ethylene glycol dimethacrylate (EGDMA), trimethylolpropane trimethacrylate (TMPTMA), triethyleneglycol dimethacrylate (TEGDMA) urethane dimethacrylates (UEDMA), having the structural formula $$H_2C=\underset{\underset{O}{\|}}{\overset{\overset{CH_3}{|}}{C}}-C-O-\underset{\underset{H\ H}{|\ |}}{\overset{\overset{H\ H}{|\ |}}{C.C}}.O-\underset{\underset{O}{\|}}{\overset{}{C}}-\underset{\overset{|}{H}}{N}-CH_2.CH.CH_2.\underset{\underset{CH_3}{|}}{\overset{\overset{CH_3}{|}}{C}}-CH_2.CH_2.\underset{\overset{|}{H}}{N}-\underset{\underset{O}{\|}}{\overset{}{C}}-O-CH_2.CH_2.O-\underset{\underset{O}{\|}}{\overset{\overset{CH_3}{|}}{C}}=CH_2$$

and (TUDMA), having the structural formula

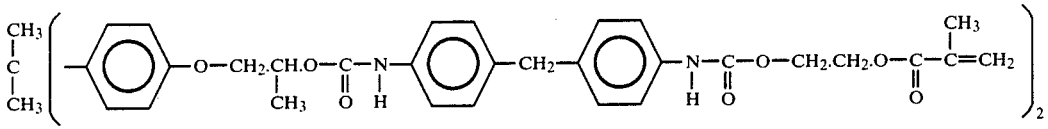

and polyethyleneglycol dimethyacrylate (poly-EGDMA). In addition to the foregoing acrylic monomers, other monomers of this type may be employed, especially as crosslinking monomers, such as diethyleneglycol dimethacrylate (DEGDMA).

When it is necessary to prepare an interpolymer, and/or a resulting composition, which is required to be particularly resistant to swelling and/or degradation resulting from aqueous imbibition, one of the comonomers should possess crosslinking properties in the resulting interpolymer. A highly cross-linked structure is advantageous when a strong adhesive is required. Also, such resins can be used in filled compositions which are suitable for bonding and as composite restoratives.

Filler material for incorporation in compositions of the present invention include all those known in the art of effecting high impact strength, resistance to moisture invasion, etc., such as exhibited by inorganic silicates as well as other fillers known in the art. These fillers include amorphous silica, glass, quartz, alumina, and apatite phosphates. In particular, glass, silica and silane-treated silica and glass have been found to be especially useful with the interpolymers described herein.

Also a preformed resin powder may be included in compositions prepared according to the invention to facilitate handling by formation of a plastic mass. Inclusion of such powder concomitantly reduces the heat produced by exothermic polymerization since the amount of polymerization is lessened, and the degree of shrinkage resulting from polymerization is reduced. Preformed resin powders useful herein include polymethacrylate (PMMA) as well as any copolymers of acrylate and/or methacrylate compatible with the other components for the intended use. See for example U.S. Pat. No. 3,427,274.

Copolymer acrylic resins for dental application are generally prepared by mixing separate portions of the monomers or comonomers either previously combined without polymerization or in uncombined portions, each of the separate portions having included therein either an initiator or an accelerator. Accordingly, each of the two components, which can be in either a liquid state, or a powder or in a paste form, are designated an accelerator portion or an initiator portion. Polymerization of the two monomer reactants occur when both the initiator and the accelerator are present. Thus, the accelerator portion and initiator portion are mixed just before application to the appropriate surface. Inasmuch as no limitation is imposed on the way in which the components are mixed, any other suitable method of combining the ingredients may be used.

In any event, initiators useful in the polymerization reaction include, but are not limited to, benzoyl peroxide, cumene hydroperoxide, etc. Such initiators are well known to those skilled in the art, and it is intended to include all useful initiators.

Similarly, accelerators used in the present invention include, but are not limited to N,N-dimethyl-p-toluidine (DMPT), dihydroxy ethyl-p-toluidine (DHEPT),1-acetyl-2-thiourea, etc., and the present invention contemplates all useful accelerators presently known in the art. See, for example, U.S. Pat. No. 3,991,008 to Temin, et al.

A third component of the present interpolymer is a polymerizable monomer which contains an anion exchange site capable of carrying a fluoride ion. When reacted in combination with the resin described above, the deposited material forms a diffusion barrier against demineralization, and supplies fluoride in controlled amounts to the oral environment immediately adjacent to the surface of the teeth over an extended period.

Even though any anion-exchange-site-bearing polymerizable monomer capable of carrying a fluoride ion can be used, it has been found that amine-substituted monomers which form weak-base and/or quaternary fluoride salts can be polymerized to form anion-exchanging resins. Typical weak-base amine-HF monomers useful herein include alkyl-aminoalkyl acrylates or methacrylates having the following general formula

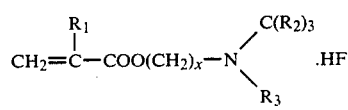

in which
$R_1$ is H or $CH_3$,
X is an integer of 1 to 12,
$R_2$ is H or an alkyl group of $C_1$ to $C_4$, and
$R_3$ is H or an alkyl group of $C_1$ to $C_{12}$.

In one embodiment of the invention the monomer t-butylaminoethyl methacrylate hydrogen fluoride (t-BAEM-HF),

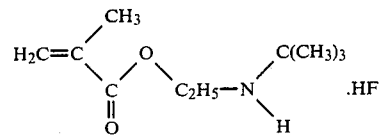

was found to be particularly effective.

Another useful monomer, which is a quaternary fluoride salt, is N,N,N,-trimethylaminoethyl-methacrylate fluoride

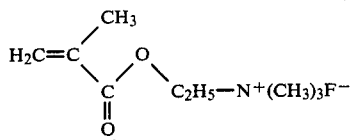

Other ingredients may be included as necessary to achieve particularly good results. For example, it has been discovered that the use of methacrylic acid is especially effective to attain a secure deposition.

It is believed that the methacrylic acid acts as a wetting/etching agent in that it alters slightly the surface of the tooth, i.e., "roughens" the surface, so that the liquid reactants will readily adhere thereto, while at the same time the methacrylic acid makes the liquid reaction mixture more compatible with the tooth surface so that the mixture readily spreads or "wets" to such surface with ease. Moreover, inclusion of methacrylic acid, which actually copolymerizes with the other monomers present during the reaction, also accelerates the polymerization reaction, a highly desirable feature for a reaction taking place in the oral environment. Consequently, when the present invention is used in a role requiring a strong bond, incorporation of methacrylic acid might eliminate the need for an intermediate acid-etching step.

Further components used in the present invention are polymerization inhibitors in very slight amounts in order to increase storage life and allow time for application to the surfaces requiring treatment before complete polymerization. Examples of such inhibitors are hydroquinones, such as butylated hydroxy toluidene (BHT) and butylated hydroxy anisole (BHA); methyl ether of hydroquinine (MEHQ) has been found to be particularly effective in the present invention.

The various acrylic materials having large molecules as previously described herein may be employed either in their monomeric or polymeric form, and, if the latter form is employed, after polymerization to a solid, as distinguished from a high viscosity high molecular weight liquid, they are ground to a powder. The other acrylic materials described herein may similarly be employed.

The anion-exchange-site-bearing polymerizable monomer (hereinafter the acrylic fluoride monomer) is employed according to the method of the the invention in one of several ways. The acrylic fluoride monomer may be admixed with acrylic materials and other acrylic monomers, such as crosslinking monomers, and cured, or may be polymerized with acrylic materials (other than the large molecule acrylic materials) and acrylic monomers that act as crossliners. The polymeric material obtained in this respect may be used in that form as an anti-caries material or may be ground to a powder-like form and admixed with polymerizable small and/or large molecule acrylic materials and that mixture in turn polymerized for use as an anti-caries material.

Additionally, the large molecule acrylic material in the monomeric form may be combined with other acrylic monomers, polymerized and the resulting polymer ground to a powder and combined with the acrylic fluoride monomer and acrylic monomers (including acrylic monomers having large molecules) and crosslinking acrylic monomers. Lastly, a monomeric mixture of the acrylic fluoride monomer, and various large molecule acrylic monomers may be polymerized in the presence of any acrylic monomer crosslinking material.

Various commercial products employing acrylic materials having bulky molecules are described in Ruyter, et al. and these formulations may be employed in combination with the acrylic fluoride monomer of the present invention as described hereinabove.

Another means of effecting polymerization of the resins of this invention is by external application of radiation, either ultraviolet or visible light. This form of curing can be accomplished either in situ or external to the body. In such applications, the initiators must be sensitive to the radiation source and produce free radicals when irradiated. Photoinitiators include benzoin derivatives such as benzoin methyl ether (sensitive to 366 nm UV radiation) and Camphoroquinone combined with tertiary amines such as N, N-dimethylaminoethyl methacrylate (sensitive to 468 nm visible radiation). Those skilled in the art will understand that any means of producing free radicals, including external radiation, can effectuate initiation and cure of the resins of this invention. Accordingly, all such means of initiation and cure are considered to be within the scope of the present invention.

EXAMPLES

Various polymers were prepared to determine the effect of large molecule acrylic materials in combination with the acrylic fluoride monomers or polymers prepared from the acrylic fluoride monomers.

The following formulations were made by a heat-curing process:

|  | FR-16 | W/W % | FR-30 | W/W % |
| --- | --- | --- | --- | --- |
| BP | 0.0048 g. | 0.15% | 0.0096 g. | 0.30% |
| MAA | 0.5 ml. | 16.11% | 0.5 ml. | 16.12% |
| TMPTMA | 0.5 ml. | 16.10% | 0.5 ml. | 16.10% |
| EGDMA | 1.5 ml. | 51.81% | 1.09 ml. | 37.67% |
| t-BAEMA.HF | 0.5 ml. | 15.85% | 0.94 ml. | 29.82% |
| MEHQ | 200 ppm. | — | 200 ppm. | — |

Each formulation was placed in an oven at 95° C. after which they formed a hard polymerized mass within about ½ hour.

Formulation of FR-16 & FR-30 self-cured:

|  | FR-16 | | | FR-30 | | |
| --- | --- | --- | --- | --- | --- | --- |
|  | A | B | w/w % | A | B | w/w % |
| BP | 0.020 g | — | 0.62% | 0.025 g | — | 0.78% |
| MAA | 0.25 ml | 0.25 ml | 15.74% | 0.25 ml | 0.25 ml | 15.75% |
| TMPTMA | 0.25 ml | 0.25 ml | 16.00% | 0.25 ml | 0.25 ml | 16.00% |
| EGDMA | 0.75 ml | 0.75 ml | 51.57% | 0.545 ml | 0.545 ml | 37.50% |
| t-BAEMA.HF | 0.25 ml | 0.25 ml | 15.78% | 0.470 ml | 0.470 ml | 29.68% |
| DMPT | — | 0.01 ml | 0.29% | — | 0.02 ml | 0.29% |
| MEHQ | 200 ppm | 200 ppm | — | 200 ppm | 200 ppm | — |

Mix 0.15 g of A & B and pour into a 1 × 10 mm mold.

The components of each formulation were kept at room temperature for about 3 hours, mixed in the proportions indicated above and cured within about 3 minutes by mixing component A with B.

Formulations of a commercial pit and fissure sealant utilizing large molecule acrylic materials were prepared and designated "DS Sealant." The components of the formulation comprised a monomer mixture designated "DS Universal" containing approximately 53% by weight of the monomer TEGDMA and 37 weight percent of the monomer bis-GMA and 5 weight percent of the monomer bis-MA along with a polymerization accelerator. This component is combined with an equal weight of a component designated "DS Catalyst" containing approximately 53 weight percent TEGDMA, 37 weight percent bis-GMA and 5 weight percent bis-MA along with an acrylic polymerization initiator.

A formulation designated DS/1.6 (corresponding to the same t-BAEMA.HF level as used in the 10% loading with FR-16 described below) was prepared as follows:

|  |  | W/W % |
|---|---|---|
| DS Universal | 0.1968 g. | 49.2% |
| DS Catalyst | 0.1968 g. | 49.2% |
| t-BAEMA.HF | 0.0064 g. | 1.6% |

A second formulation was prepared designated DS/3.0. This corresponds to t-BAEMA.HF level used with the 10% loading of FR-30 described below. DS/3.0 utilized the following materials:

|  |  | W/W % |
|---|---|---|
| DS Universal | 0.1940 g. | 48.5% |
| DS Catalyst | 0.1940 g. | 48.5% |
| t-BAEMA.HF | 0.012 g. | 3.0% |

A third formulation was also prepared without incorporating t-BAEMA.HF as follows:

|  |  | W/W % |
|---|---|---|
| DS Universal | 0.075 g. | 50.0% |
| DS Catalyst | 0.075 g. | 50.0% |

The various formulations noted immediately above were mixed and cured at room temperature within about 1-2 minutes after being poured into a 1 by 10 millimeter mold.

The various formulations were then prepared in which the DS Sealant was loaded with pulverised FR-16 resin, FR-30 resin or polymerized DS sealant.

A mixture was formed of 0.7 g of DS Universal with 0.1556 g. of 64-88 micron powdered resins FR-16, FR-30 or polymerized DS Sealant.

Each of the mixtures was placed in a vacuum overnight. Afterwards, 0.1222 g. of this mixture was combined with 0.100 g. of DS Catalyst and mixed for 20 seconds after which each of the mixtures was poured into a 1 by 10 millimeter mold, covered and cured in about 1-2 minutes.

By utilizing the foregoing procedures, 1 by 10 millimeter pellets of the following compositions are obtained.

1. DS sealant made with DS Universal and DS Catalyst only.
2. DS sealant made with 1.6% t-BAEMA.HF corresponding to a 10% loading with FR-16.
3. DS sealant containing 3% t-BAEMA.HF corresponding to a 10% loading with FR-30.
4. DS sealant containing 10% by weight of 64-88 micron DS sealant powder.
5. DS sealant containing 10% by weight 64-88 micron FR-16 powder.
6. DS sealant containing 10% by weight 64-88 micron FR-30 powder.
7. FR-16 self cured.
8. FR-30 self cured.

Each of the above pellets was placed in a 100% relative humidity environment at 37° C. overnight and weight and hardness of each determined. The pellets were then placed in 10 milliliters of 0.2M sodium chloride and the pellets in solution were then positioned in a shaker bath that was kept at 37° C. Fluoride ion readings were made and the sodium chloride solution changed at intervals of 15 minutes, ½ hour, 45 minutes, 1 hour, 1½ hours, 2 hours, 4 hours, 24 hours, 48 hours, 5 days, 1, 2, 3, 4, 6, 8, 12 and 16 week intervals. The hardness was checked at 24 hours, 1 week, 2 week, 1 month, 2 month, 3 month and 4 month intervals.

Figure 2:
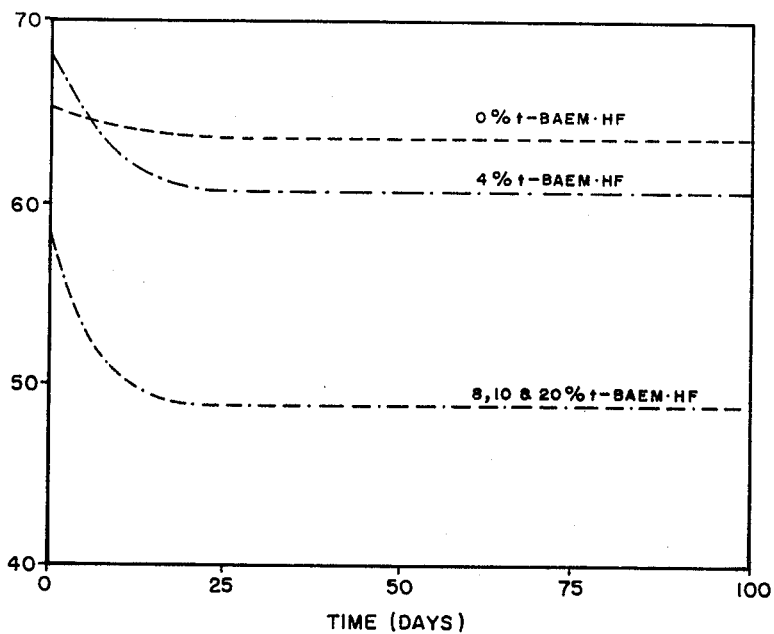
Figure 3:
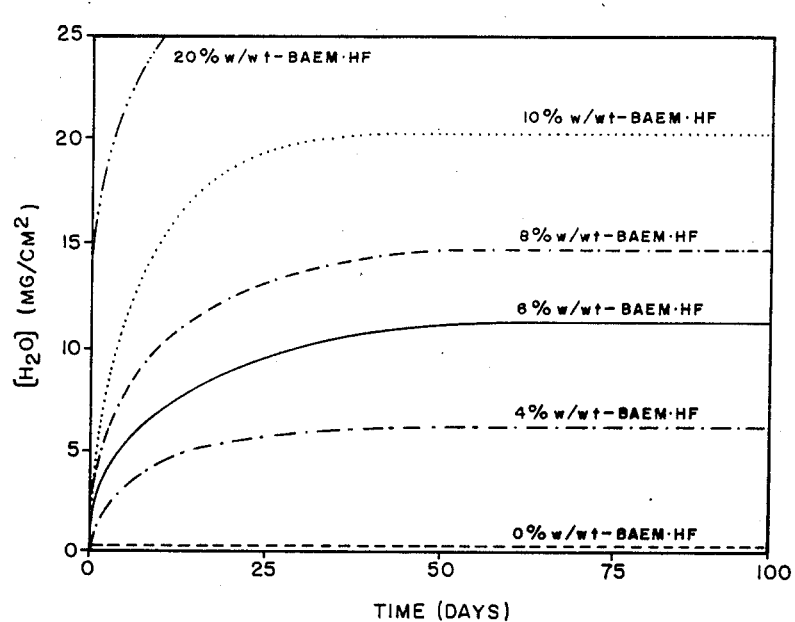
FIG. 3 is a graph showing the weight change of the interpolymers of the present invention.
Figure 4:
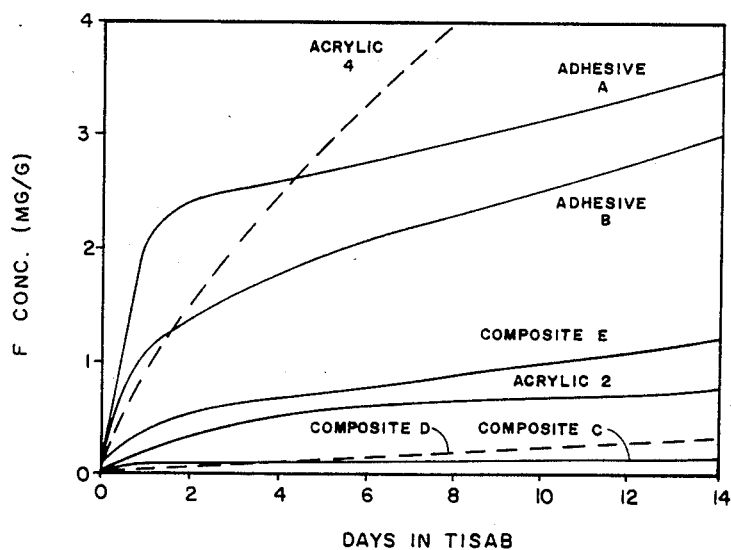
FIG. 4 is a graph showing the knoop hardness of the interpolymers of the present invention.

The results obtained are set forth in the attached FIGS. 1-4.

An additional acrylic controlled, fluoride-releasing interpolymer was prepared from bis-EMA, bis-MA and TEGDMA. Formulations were prepared for both interpolymers which are to incorporate fillers and interpolymers which may be used without filler materials. The filler is added from about 5 to about 90 percent by weight of the total formulation. The preferred ranges for the formulations, and parts by weight are given below. Benzoyl peroxide is used as the polymerization initiator in an amount from about 0.5 to about 3.0 percent by weight, and an accelerator comprising either N,N- dimethyl-p-toluidine or DHEPT from about 0.5 to about 3.0 percent by weight is employed and the compositions cured at ambient temperatures. The resins harden within about one-half minute to about five minutes. The preferred ranges for the various components are set forth below.

| COMPONENT | PREFERRED RANGE FOR UNFILLED RESINS | FILLED RESINS |
|---|---|---|
| Fluoride monomer* | 2-10 | 2-10 |
| Bis-EMA** | 30-45 | 40-75 |
| Bis-MA | 0-5 | 4-9 |
| TEGDMA*** | 68-38 | 54-4 |
| MAA | 0-2 | 0-2 |

*t-BAEMA-HF, DMAEMA-HF, DEAEMA-HF(N,N—diethylamino ethyl methacrylate) or quaternary fluoride salts of DMAEMA and DEAEMA.
**Bis-GMA may be substituted for all or a portion of Bis-EMA.
***triethyleneglycol dimethacrylate It has been found that by using bis-EMA rather than bis-GMA, a reduction of the overall cured-resin hydrophilicity is obtained. This helps to offset the hydrophilic nature of the fluoride monomers. Degradation in physical properties is reduced with this substitution, due to the lower degree of moisture imbibition uptake. Crazing and discoloration are minimized as well.

In the foregoing experiments, it has also been discovered that by employing dimethylaminoethyl methacrylate hydrogen fluoride (DMAEMA-HF) as the acrylic fluoride monomer, the interpolymer formed therefrom according to the invention has lower initial color than interpolymers prepared from t-BAEMA.HF.

In summation, the present invention provides a new resin and composition, as well as a method for treating teeth which forms a protective barrier for the surface of the tooth and supples a source of fluoride ions for controlled release.

Thus, while there have been described what are presently believed to be the preferred embodiments of the invention, those skilled in the art will realize that changes and modifications may be made thereto without departing from the spirit of the invention and it is intended to claim all such changes and modifications as fall within the true scope of the invention.

What is claimed is:

1. An acrylic, controlled-fluoride-releasing interpolymer comprising the reaction product of:

a. an anion-exchange-site bearing monomer carrying a fluoride ion in an amount sufficient to provide a caries-inhibiting amount of fluoride;

b. a copolymerizable acrylic monomer selected from the group consisting of bis-MA; bis-GMA; bis-EMA; bis-PMA; UEDMA; TUDMA, c-HaDMA; c-HeDMA;

c. a monomer which forms a cross-link in the resulting interpolymeric resin.

2. The interpolymer of claim 1 wherein said acrylic monomer comprises bis-GMA.

3. The interpolymer of claim 1 wherein said acrylic monomer comprises bis-MA.

4. The interpolymer of claim 1 wherein said acrylic monomer comprises bis-EMA.

5. The interpolymer of claim 1 wherein said acrylic comprises bis-PMA.

6. The interpolymer of claim 1 wherein said acrylic monomer comprises UEDMA.

7. The interpolymer of claim 1 wherein said acrylic monomer comprises TUDMA.

8. The interpolymer of claim 1 wherein said acrylic monomer comprises c-HeDMA.

9. The interpolymer of claim 1 wherein said acrylic monomer comprises c-HaDMA.

10. The interpolymer of claim 1 which further comprises a wetting/etching monomer.

11. The interpolymer of claim 10 wherein said wetting/etching monomer is methacrylic acid.

12. The interpolymer of claim 1 wherein said acrylic monomer is included in an amount of from about 10% to about 99% based on the volume of unfilled prepolymerization reaction mixture.

13. The interpolymer of claim 12 wherein said amount is from about 50% to about 75%.

14. The interpolymer of claim 1 wherein said fluoride carrying monomer is included in an amount of from about 1% to about 40% based on the volume of unfilled prepolymerized reaction mixture.

15. The interpolymer of claim 14 wherein said amount is from about 10% to about 30%.

16. The interpolymer of claim 1 wherein said monomeric crosslinker is selected from the group consisting of ethylene glycol dimethacrylate, trimethylolpropane trimethyacrylate, triethylene glycol dimethacrylate, diethylene glycol dimethacrylate, and polyethylene glycol dimethacrylate.

17. The interpolymer of claim 16 wherein said crosslinker is included in said interpolymer in an amount of from about 0.5% to about 80% based on the volume of unfilled prepolymerization reaction mixture.

18. The interpolymer of claim 17 wherein said amount is from about 10% to about 25%.

19. The interpolymer of claim 1 wherein said fluoride carrying monomer is selected from the group consisting of the quaternary fluoride salt of an aminoalkylacrylate, the hydrogen fluoride salt of an aminoalkylacrylate, the quaternary fluoride salt of an aminoalkylmethacrylate and the hydrogen fluoride salt of an aminoalkylmethacrylate.

20. The interpolymer of claim 19 wherein said aminoalkylacrylates and said aminoalkylmethacrylates have the general formula:

$$CH_2=C(R_1)-COO(CH_2)_x-N(C(R_2)_3)(R_3)$$

in which
$R_1$ is H or $CH_3$,
X is an integer of 1 to 12,
$R_2$ is H or an alkyl grop of $C_1$ to $C_4$ and
$R_3$ is H or an alkyl group of $C_1$ to $C_{12}$.

21. The interpolymer of claim 20 wherein said monomer is DMAEMA.HF.

22. The interpolymer of claim 20 wherein said monomer is DEAEMA.HF.

23. A composition of matter comprising the interpolymer of claim 20 which is highly crosslinked and a filler in an amount of from about 5 to about 90% based on the total weight of said composition.

24. The composition of matter of claim 23 wherein said filler is an inorganic silicate.

25. The composition of matter of claim 23 wherein said filler is one of apatite phosphates, silica, glass, quartz, alumina or silanized versions thereof.

26. The interpolymer of claim 1 wherein said acrylic fluoride containing monomer is t-butylaminoethyl methacrylate hydrogen fluoride.

27. The interpolymer of claim 1 wherein said acrylic fluoride containing monomer is N,N, N-trimethylamino ethylmethacrylate fluoride.

28. A method of preventing dental caries comprising impregnating a tooth with the interpolymer of claim 1.

29. A method of preventing dental caries comprising impregnating a tooth with the interpolymer of claim 1 and a polyalkylacrylate.

30. A method of preventing dental caries comprising depositing the composition of claim 1 on a tooth.

31. A method of preventing dental caries comprising use of a fixed or removable oral device fabricated by use of the interpolymer of claim 1.

* * * * *

UNITED STATES PATENT AND TRADEMARK OFFICE
CERTIFICATE OF CORRECTION

PATENT NO. : 4,572,920

DATED : February 25, 1986

INVENTOR(S) : Henry A. Rawls, et al.

It is certified that error appears in the above-identified patent and that said Letters Patent is hereby corrected as shown below:

Column 4, line 2: After "invention" insert --during storage in 0.2M sodium chloride--.

Column 4, line 4: After "invention" insert --after 3 months in 0.2M sodium chloride--.

Column 8, line 47: In the table under heading FR-30, B, corresponding to DMPT, "0.02ml" should be --0.01--.

In the Claims:

Claim 26: delete --acrylic--.

Claim 27: delete --acrylic--.

Signed and Sealed this

Twentieth Day of January, 1987

*Attest:*

DONALD J. QUIGG

*Attesting Officer*   *Commissioner of Patents and Trademarks*